United States Patent [19]

Rodder

[11] 4,259,968

[45] Apr. 7, 1981

[54] BIPOLAR FLUID MEASURING APPARATUS

[76] Inventor: Jerome A. Rodder, 775 Sunshine Dr., Los Altos, Calif. 94022

[21] Appl. No.: 936,380

[22] Filed: Aug. 24, 1978

Related U.S. Application Data

[63] Continuation-in-part of Ser. No. 809,302, Jun. 23, 1977, Pat. No. 4,163,390, which is a continuation-in-part of Ser. No. 787,467, Apr. 14, 1977, abandoned.

[51] Int. Cl.$^3$ .............................................. A61B 5/08
[52] U.S. Cl. .................................... 128/724; 128/725; 73/204
[58] Field of Search ............... 128/724, 725, 716, 718, 128/719; 73/204, 205, 196, 202, 194 VS

[56] References Cited

U.S. PATENT DOCUMENTS

| | | | |
|---|---|---|---|
| 3,091,113 | 5/1963 | Nerheim | 73/204 X |
| 3,452,595 | 7/1969 | Auger | 73/204 |
| 3,613,448 | 10/1971 | Benson et al. | 73/204 X |
| 3,691,830 | 9/1972 | Tomata | 73/194 VS |
| 3,735,752 | 5/1973 | Rodder | 128/724 |
| 3,949,739 | 4/1976 | Rodder | 128/725 |
| 3,962,917 | 6/1976 | Terada | 128/725 X |

OTHER PUBLICATIONS

Ohl, "Ventitrol, A New Apparatus . . . vol. In Unit Time", Proceeding of the 1st Nordic Meeting on Med. and Biol. Eng., Otaniemi, Finland, Jen 1970, pp. 35-37.

Primary Examiner—Lee S. Cohen
Attorney, Agent, or Firm—Christie, Parker & Hale

[57] ABSTRACT

In a spirometer, a breath transmission passage has first and second ends open to the atmosphere and a given cross-sectional area. A patient breathes through the breath transmission passage bidirectionally. An elongated conduit has a first port at one end, a second port at the other end, and a third port intermediate to the first and second ports to form a first flow measurement passage in the conduit between the first and third ports and a second flow measurement passage in the conduit between the second and third ports. The first and second flow measurement passages have a substantially smaller cross-sectional area than the given cross-sectional area. The breath transmission passage at a point near the first end is coupled by a removable connection to the first port, and the breath transmission passage at a point near the second end is coupled by a removable connection to the second port. The flow resistance between the first end of the breath transmission passage and the third port equals the flow resistance between the second end of the breath transmission passage and the third port. A source of bias gas is connected to the third port. The difference between the rate of gas flow through the first and second flow measurement passages responsive to inhalation from and exhalation to the breath transmission passage is sensed to provide a balanced bipolar indication thereof. In one embodiment, a vacuum pump is disposed between the removable connections and the first and third ports.

16 Claims, 4 Drawing Figures

BIPOLAR FLUID MEASURING APPARATUS

CROSS REFERENCE TO RELATED APPLICATIONS

This is a continuation-in-part of my application Ser. No. 809,302, filed June 23, 1977, now Pat. No. 4,163,390 which is a continuation-in-part of my application Ser. No. 787,467, filed Apr. 14, 1977, now abandoned.

BACKGROUND OF THE INVENTION

This invention relates to apparatus for measuring bipolar fluid flow and, more particularly, to such apparatus especially well suited for use as a spirometer.

My U.S. Pat. No. 3,735,752, which issued May 29, 1973, discloses a spirometer comprising a breath transmission passage in which a venturi is formed, and a flow measurement passage that communicates at one end with the throat of the venturi and at the other end with the atmosphere. Air flow through the breath transmission passage creates a subatmospheric pressure at the throat of the venturi to aspirate air from the atmosphere through the flow measurement passage. Apparatus such as a thermistor bead or a hot wire electrically connected into one arm of a bridge circuit measures the flow rate through the flow measurement passage, which is dependent upon the flow rate through the breath transmission passage. Bias gas, i.e., dry air is preferably supplied to the breath transmission passage to ensure that the moisture does not reach the flow rate measuring apparatus in the flow measurement passage. Such moisture would have a deleterious affect on the accuracy of the measurement and tend to corrode a hot wire.

In the described spirometer, the flow of breath through the breath transmission passage draws air from the atmosphere through the flow measurement passage irrespective of the direction of flow through the breath transmission passage to cool the hot wire or thermistor. As a result, the electrical output from the bridge circuit does not distinguish between inhalation and exhalation.

In the case of children, the total breathing flow rate is so small that the bias gas may appreciably affect the composition of the patient gas supplied by a respirator, particularly the percentage of water in such patient gas. Further, the patient gas inhaled by the patient may contain too much of the patient's breath from his preceding exhalation.

SUMMARY OF THE INVENTION

The invention provides a bipolar electrical signal responsive to bidirectional gas flow, i.e., breathing, through a breath transmission passage—one polarity for inhalation and the other polarity for exhalation.

The breath transmission passage has first and second ends open to the atmosphere. An elongated conduit has a first port at one end, a second port at the other end, and a third port intermediate to the first and second ports to form a first flow measurement passage in the conduit between the first and third ports, and a second flow measurement passage in the conduit between the second and third ports. The breath transmission passage at a point near the first end is interconnected to the first port, and the breath transmission passage at a point near the second end is interconnected to the second port. A source of bias gas is connected to the third port. There is generated a bipolar electrical signal dependent upon the difference between the rate of gas flow through the first and second flow measurement passages responsive to patient inhalation from and exhalation to the breath transmission passage. The flow resistance between the first end of the breath transmission passage and the third port equals the flow resistance between the second end of the breath transmission passage and the third port, thereby balancing the bipolar signal in the absence of flow through the breath transmission passage.

According to a feature of the invention, the breath transmission passage has a given cross-sectional area that is larger than that of the flow measurement passages. Removable connections are provided between the breath transmission passage and the first and second ports to permit substitution of breath transmission passages having different given cross-sectional areas suitable for the lung capacity of the patient.

BRIEF DESCRIPTION OF THE DRAWINGS

The features of specific embodiments of the best mode contemplated of carrying out the invention are illustrated in the drawings, in which.

DETAILED DESCRIPTION OF THE SPECIFIC EMBODIMENTS

Figure 1:
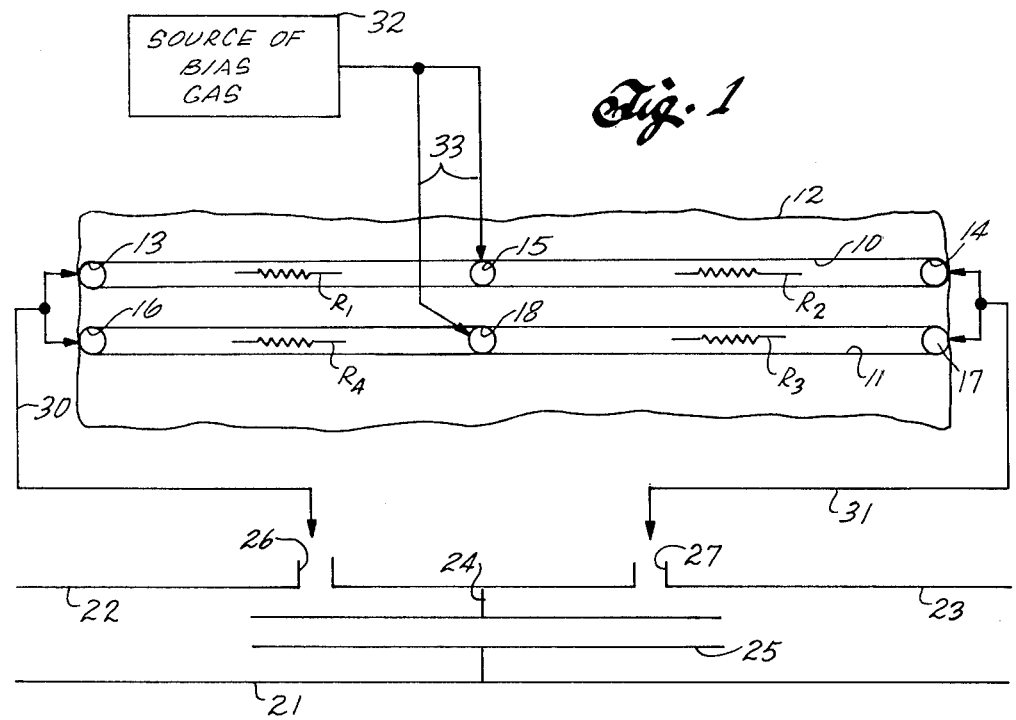
FIG. 1 is a schematic diagram of an embodiment of a spirometer for adults and larger children incorporating the principles of the invention.

In FIG. 1, a straight elongated conduit 10 and a straight elongated conduit 11 are formed in a housing 12 made of a block of material having high thermal conductivity such as aluminum or steel to make the apparatus thermally stable. Conduit 10 has ports 13 and 14 at its ends, and a port 15 midway between ports 13 and 14 to form a pair of flow measurement passages. Conduit 11 has ports 16 and 17 at its ends, and a port 18 midway between ports 16 and 17 to form another pair of flow measurement passages. A blow tube or breath transmission passage 21 has ends 22 and 23 open to the atmosphere. Midway between ends 22 and 23, a partition 24 extends across breath transmission passage 21. A tube 25 having a substantially smaller diameter than breath transmission passage 21, passes through partition 24 to provide communication between ends 22 and 23. Tube 25 serves as a restriction on air flow between ends 22 and 23. Alternatively, partition 24 and tube 25 can be eliminated, leaving an unrestricted channel between ends 22 and 23.

Breath transmission passage 21 has an intermediate port 26 between end 22 and partition 24, and an intermediate port 27 between end 23 and partition 24. Intermediate port 26 is interconnected to ports 13 and 16 by flexible tubing, designated 30, and intermediate port 27 is interconnected to ports 14 and 17 by flexible tubing, designated 31. Preferably, intermediate ports 26 and 27 are located near the restriction, i.e., between the ends of tube 25 and partition 24 as illustrated in FIG. 1, where the gas velocity is low, and thus the turbulence is small. In the case of an unrestricted channel in breath transmission passage 21, intermediate ports 26 and 27 are located near ends 22 and 23, respectively. Tubing 30 and 31 comprises removable connections between breath transmission passage 21 and housing 12 in that they can be removed from intermediate ports 26 and 27, which could be cylindrical tee fittings, for the purpose of interchanging or substituting breath transmission passages. A breath transmission passage having a suitable cross-sectional area for the lung capacity of the particular patient is selected and connected to tubing 30 and 31. If the cross-sectional area of breath transmission passage 21 is too large for the patient, the sensitivity of the measurement is impaired. If the cross-sectional area of the breath transmission passage is too small for the patient, the resistance to flow of breath is too large for accurate measurement. The cross-sectional area of the breath transmission passage, which is in general substantially larger than the cross-sectional area of conduits 10 and 11 and tubing 30 and 31, should be just large enough to pass the patient's breath without appreciable resistance to flow, whether or not a restriction is formed in the breath transmission passage.

A source 32 of bias gas, i.e., dry air under pressure, is connected to ports 15 and 18 by flexible tubing designated 33. Source 32 supplies gas at a sufficiently high, preferably constant, flow rate to prevent flow from breath transmission passage 21 through conduits 10 and 11 when a patient breathes through breath transmission passage 21. The difference in cross-sectional area between breath transmission passage 21 and conduits 10 and 11 further inhibits the patient's breath from reaching conduits 10 and 11.

Conduits 10 and 11 form in effect a fluid bridge comprising, as a first arm, the flow measurement passage between ports 15 and 13, as a second arm, the flow measurement passage between ports 18 and 16, as a third arm, the flow measurement passage between ports 15 and 14, and, as a fourth arm, the flow measurement passage between ports 18 and 17. The flow resistance between ports 15 and 26 approximately equals the flow resistance between ports 15 and 27. The flow resistance between ports 18 and 26 approximately equals the flow resistance between ports 18 and 27. Thus, in the absence of breath flow through breath transmission passage 21, the fluid bridge is approximately balanced, i.e., the same rate of bias gas from source 32 flows through each flow measurement passage.

When a patient exhales into end 22 of breath transmission passage 21, there is a pressure drop from end 22 to end 23 by virtue of the restriction provided by tube 25. Consequently, the pressure at ports 13 and 16 rises to unbalance the fluid bridge. The bias gas flowing through the flow measurement passages between ports 15 and 13 and ports 18 and 16 decreases, and the bias gas flowing through the flow measurement passages between ports 15 and 14 and ports 18 and 17 increases.

When the patient inhales from end 22 of breath transmission passage 21, there is a pressure drop from end 23 to end 22 by virtue of the restriction provided by tube 25. Consequently, the pressure at ports 14 and 17 rises to unbalance the fluid bridge. The bias gas flowing through the flow measurement passages between ports 15 and 14 and ports 18 and 17 decreases, and the bias gas flowing through the flow measurement passages between ports 15 and 13 and ports 18 and 16 increases.

Exhalation into end 23 of breath transmission passage 21 produces the same effect as inhalation from end 22, and inhalation from end 23 from breath transmission passage 21, produces the same effect as exhalation into end 22. Thus, the fluid bridge is balanced in the absence of breathing through the breath transmission passage, and becomes bidirectionally unbalanced responsive to bidirectional breathing through the breath transmission passage.

When the breath transmission passage does not have a restriction, although a much smaller pressure drop results between intermediate ports 26 and 27, the fluid bridge becomes unbalanced in the same manner described above in response to bidirectional breathing through the breath transmission passage.

Breath transmission passage 21, tube 25 if used, conduits 10 and 11, and tubing 30 and 31 are designed so there is substantially more flow resistance presented by the flow path through conduits 10 and 11 than the flow path through tube 25. For example, in the absence of bias gas, about 95 percent of the gas flowing into end 22 or end 23 flows through tube 25, and about 5 percent thereof flows through conduits 10 and 11. To increase or decrease the breath flow rate to which the apparatus of FIG. 1 responds, it is simply necessary to substitute a breath transmission passage having a larger or smaller cross-sectional area for breath transmission passage 21.

To measure the flow rate of air passing through tube 25 in response to patient breathing through breath transmission passage 21, the difference between the rate of gas flow through the flow measurement passages between ports 15 and 14 and ports 18 and 17, and the flow measurement passages between ports 15 and 13 and ports 18 and 16 is sensed. Preferably, hot wires designated $R_1$, $R_2$, $R_3$, and $R_4$, in FIG. 1 are employed as sensors. Hot wire $R_1$ extends along the length of the flow measurement passage between ports 15 and 13, hot wire $R_2$ extends along the length of the flow measurement passage between ports 15 and 14, hot wire $R_3$ extends along the length of the flow measurement passage between ports 18 and 17, and hot wire $R_4$ extends along the length of the flow measurement passage between ports 18 and 16.

Figure 2:
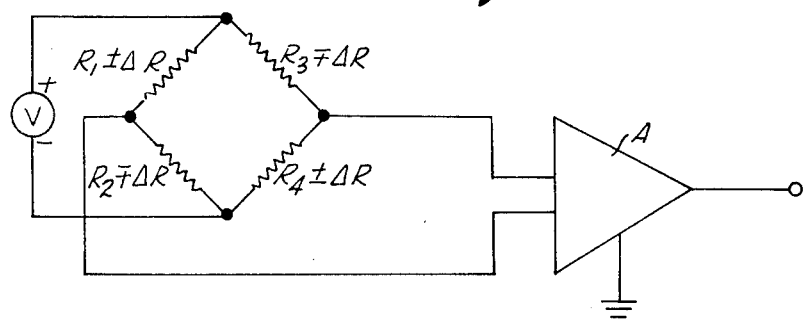
FIG. 2 is an electrical schematic diagram depicting the electrical connections of the hot wires in the spirometer of FIG. 1.

As shown in FIG. 2, hot wires $R_1$ through $R_4$ serve as arms of an electrical bridge. Hot wires $R_1$ and $R_2$ are connected in series between the output terminals of a voltage source V, with hot wire $R_1$ connected to the positive output terminal and hot wire $R_2$ connected to the negative output terminal. Hot wires $R_3$ and $R_4$ are connected in series between the output terminals of voltage source V with hot wire $R_3$ connected to the positive output terminal and hot wire $R_4$ connected to the negative output terminal. The output of the bridge, which appears between the junction of hot wires $R_1$ and $R_2$ and the junction of hot wires $R_3$ $R_4$, is coupled to an amplifier A. Air flow through breath transmission passage 21 changes the resistance of each of hot wires $R_1$ through $R_4$, as represented by R in FIG. 2. As represented by the plus and minus signs in FIG. 2, the resistance of hot wires $R_1$ and $R_4$ changes in the same direction, and the resistance of hot wires $R_2$ and $R_3$ changes in the same direction and in the opposite direction from the resistance of hot wires $R_1$ and $R_4$. Specifically, responsive to patient exhalation into end 22 of breath tranmission passage 21, the resistance of hot wires $R_1$ and $R_4$ increases because of the decreased flow rate of bias air through the flow measurement passages in which such hot wires are located, and the resistance of hot wires $R_2$ and $R_3$ decreases because of the increased bias flow rate through the flow measurement passages in which such hot wires are located. This produces a signal of positive polarity across the output terminals of the bridge, referenced to the lower output terminal. Conversely, responsive to patient inhalation from end 22 of breath transmission passage 21, the resistance of hot wires $R_1$ and $R_4$ decreases, and the resistance of hot wires $R_3$ and $R_2$ increases. This produces a signal of negative polarity across the output terminals of the bridge, referenced to the lower output terminal. As previously mentioned, the fluid bridge is approximately balanced by the approximately equal fluid resistance of its arms. In order to provide a precise null or zero output when no gas is flowing through breath transmission passage 21, a small compensating resistor may be inserted in one of the arms of the electrical bridge of FIG. 2, or a small offset may be introduced into amplifier A. In summary, the hot wires in all four arms of the bridge operate in push-pull fashion to produce a large signal in response to gas flow through breath transmission passage 21. Such signal is representative in polarity and magnitude to the direction of such flow and the rate of such flow, respectively.

With one exception, the apparatus of FIG. 1 is preferably constructed in the manner disclosed in my copending application, Ser. No. 787,468, filed Apr. 14, 1977, now U.S. Pat. No. 4,109,510, and entitled FLUID MEASURING APPARATUS. That exception is as described in connection with FIG. 3 of my copending application, Ser. No. 809,302, filed June 23, 1977. The disclosures of these applications are incorporated fully herein by reference.

Figure 3:
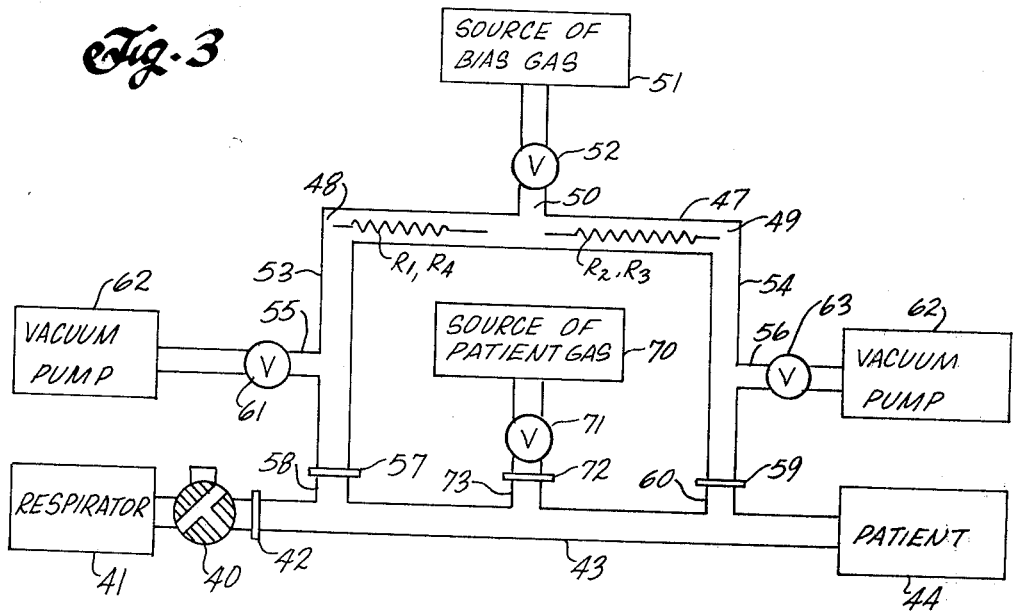
FIG. 3 is a schematic diagram of another embodiment of a spirometer for small children incorporating the principles of the invention.

In FIG. 3, a three-way valve 40 has a first port connected to a conventional respirator 41, a second port vented to the atmosphere, and a third port coupled by a removable connection 42, such as for example a threaded fitting, to one end of an unrestricted breath transmission passage or blow tube 43. Respirator 41 could provide regularly occurring pulsations of air or other gas mixtures suitable for breathing, or could provide such gas only in response to patient inhalation. A patient represented by a block 44 breathes into and out of the other end of blow tube 43. A long conduit 47, which could be formed as a channel in a block of material as described in application Serial No. 787,468, has end ports 48 and 49 and an intermediate port 50 located midway between ports 48 and 49. Between ports 48 and 50, conduit 47 forms a first long straight flow measurement passage in which hot wires $R_1$ and $R_4$ are disposed. Between ports 49 and 50, conduit 47 forms a second long straight flow measurement passage in which hot wires $R_2$ and $R_3$ are disposed. Hot wires $R_1$, $R_2$, $R_3$, and $R_4$ are connected to form an electrical bridge, as shown in FIG. 2. A source of bias gas 51 is connected by a needle valve 52 to port 50. The bias gas is preferably free of water, e.g., dry air. Conduits 53 and 54 have centrally located tee connections 55 and 56, respectively. At one end, conduit 53 is permanently connected to port 48, and at the other end it is coupled by a removable connection 57 to a tee connection 58 formed near one end of blow tube 43. At one end, conduit 54 is permanently connected to port 49, and at the other end it is coupled by a removable connection 59 to a tee connection 60 formed near the other end of blow tube 43. Tee connection 55 is coupled by a needle valve 61 to a vacuum pump 62. Tee connection 56 is coupled by a needle valve 63 to vacuum pump 62. A source of patient gas 70 is coupled by a needle valve 71 and a removable connection 72 to a tee connection 73 formed at the center of blow tube 43. The composition of patient gas from source 70 is the same as the gas supplied by respirator 41. When valve 40 is positioned to connect respirator 41 to blow tube 43, respirator 41 supplies pulsating patient gas to aid the patient's breathing. When valve 40 is positioned to vent blow tube 43, the patient exhales into and inhales from blow tube 43, unaided by respirator 41.

In operation, valve 40 is positioned to vent blow tube 43 and, in the absence of a patient, needle valves 52, 61, 63, and 71 are adjusted to provide the desired gas flow to balance the fluid bridge. For example, source 51 could provide 100 cc/min of bias gas, and source 70 could provide 100 cc/min of patient gas. The patient gas from source 70 divides in half at tee connection 73, 50 cc/min flowing through blow tube 43 and conduit 53 to vacuum pump 62, and 50 cc/min flowing through blow tube 43 and conduit 54 to vacuum pump 62. The bias gas from source 51 divides in half at port 50, 50 cc/min flowing through conduit 47 past hot wires $R_1$ and $R_4$ and conduit 53 to vacuum pump 62, and 50 cc/min flowing through conduit 47 past hot wires $R_2$ and $R_3$ and conduit 54 to vacuum pump 62. Needle valves 52, 61, 63, and 71 provide sufficiently small restrictions relative to the superatmospheric pressure of sources 51 and 70 and the subatmospheric pressure of pump 62 so that gas is supplied to port 50 and tee connection 73 at an approximately constant flow rate, and gas is withdrawn from tee connections 55 and 56 at an approximately constant flow rate, as the fluid bridge becomes unbalanced. When the patient exhales through blow tube 43, gas flows therethrough from right to left as viewed in FIG. 3. As a result, the flow rate through tee connection 58 and conduit 53 to vacuum pump 62 decreases, e.g., to 5 cc/min, the bias gas from source 51 flowing through conduit 47 past hot wires $R_1$ and $R_4$ and conduit 53 to vacuum pump 62 increases correspondingly, e.g., to 95 cc/min, the flow rate through tee connection 60 and conduit 54 to vacuum pump 62 increases correspondingly, e.g., to 95 cc/min, and the flow rate of bias gas from source 51 through conduit 47 past hot wires $R_2$ and $R_3$ and conduit 54 to vacuum pump 62 decreases correspondingly, e.g., to 5 cc/min. This unbalance of the fluid bridge produces an electrical output of one polarity, e.g., positive polarity, at the output of amplifier A. When the patient inhales from blow tube 43, gas flows therethrough from left to right as viewed in FIG. 3. As a result, the fluid bridge becomes unbalanced in the other direction, i.e., more gas flows in conduit 47 past hot wires $R_2$ and $R_3$ and from tee connection 58 through conduit 53, while less gas flows through conduit 47 past hot wires $R_1$ and $R_4$ and from tee connection 60 through conduit 54. An electrical output signal of opposite polarity, e.g., negative polarity, is produced at the output of amplifier A.

By virtue of vacuum pump 62, there is no mixing of bias gas and patient gas from source 70 and respirator 41 or the atmosphere. Thus, the moisture of the gas from respirator 11 or the atmosphere does not reach hot wires $R_1$, $R_2$, $R_3$, and $R_4$, and the moisture-free gas from source 51 does not upset the compositional balance of the patient gas from source 70 or respirator 41.

The breath exhaled by the patient is swept by patient gas from source 70 to vacuum pump 62, thereby leaving a small amount of exhaled gas for rebreathing by the patient during the next inhalation. Such rebreathed gas is objectionable because it changes the composition of the gas breathed in by a small child. Source 70 could be eliminated if this rebreathed gas does not need to be reduced in a particular setting, such as where the patient is an adult.

A new blow tube having a suitable cross-sectional area for the particular patient can easily be substituted for blow tube 43 by removing connections 42, 57, 59, and 72.

Figure 4:
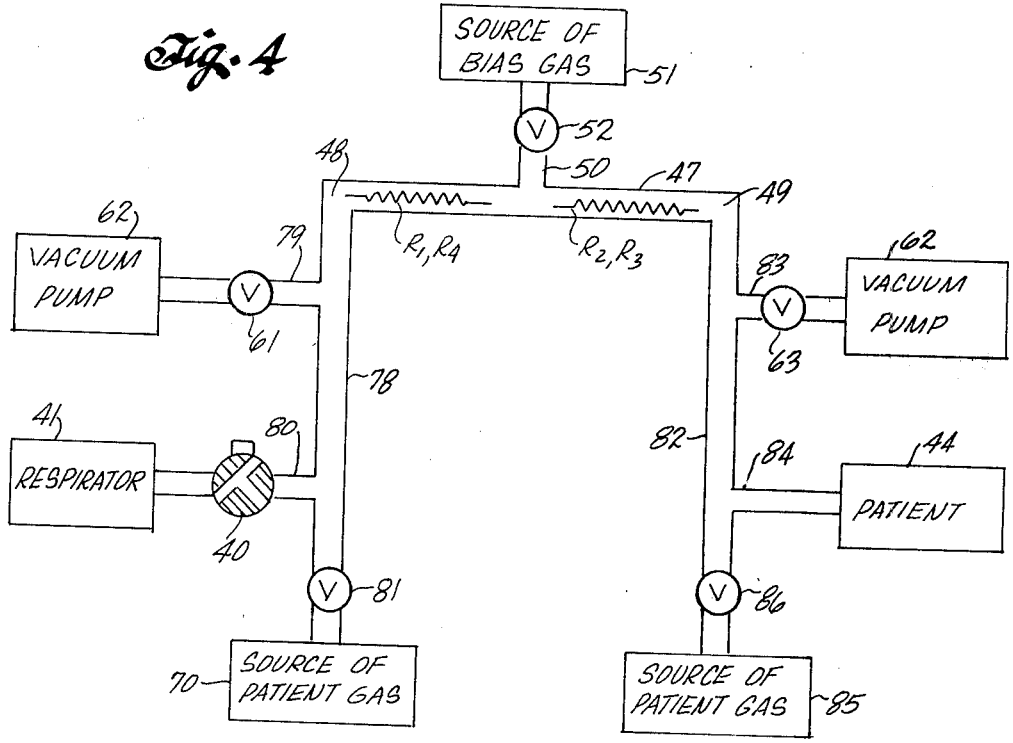
FIG. 4 is a schematic diagram of yet another embodiment of a spirometer for premature infants and small animals incorporating the principles of the invention.

In the embodiment of FIG. 4, the elements in common with the embodiment of FIG. 3 bear the same reference numerals and letters. A conduit 78 has an intermediate tee connection 79 to which vacuum pump 62 is coupled by needle valve 61 and an intermediate tee connection 80 to which respirator 41 is coupled by three-way valve 40. One end of conduit 78 is permanently connected to port 48. Source 70 is coupled by a needle valve 81 to the ther end of conduit 78. A conduit 82 has an intermediate tee connection 83 to which vacuum pump 62 is coupled by needle valve 63 and an intermediate tee connection 84 into which the patient exhales and from which the patient inhales. One end of conduit 82 is permanently connected to port 49. A source 85 of patient gas is coupled by a needle valve 86 to the other end of conduit 82. This embodiment operates in the same manner described above in connection with FIG. 3. The embodiment of FIG. 4 has all of the above enumerated advantages of the embodiment of FIG. 3, and is also more sensitive because the blow tube is, in essence, bifurcated and connected in series with conduit 47, which makes this embodiment suitable for use by premature infants and small animals.

In both the embodiments of FIGS. 3 and 4, the bias gas is adjusted to be greater than the maximum pulsating flow rate of the respirator so as to prevent patient gas from entering conduit 47 where the hot wires are located.

The described embodiment of the invention is only considered to be preferred and illustrative of the inventive concept; the scope of the invention is not to be restricted to such embodiment. Various and numerous other arrangements may be devised by one skilled in the art without departing from the spirit and scope of this invention. For example, although use of hot wires in each arm of the bridge is preferable, simple bridge balancing resistors could be substituted for hot wires $R_3$ and $R_4$. Alternatively, instead of hot wires, bead type thermistors could be employed, or some other means for sensing the difference in fluid flow rate through the arms of the fluid bridge. The whole system could be pressurized by placing tube 25 in series with a pressurized line rather than having ends 22 and 23 open to the atmosphere.

What is claimed is:

1. A spirometer comprising a breath transmission passage having first and second ends; an elongated conduit having a first port at one end, a second port at the other end, and a third port intermediate to the first and second ports to form a first flow measurement passage in the conduit between the first and third ports and a second flow measurement passage in the conduit between the second and third ports; first means for interconnecting the breath transmission passage at a point near the first end to the first port, the first interconnecting means comprising a first connecting conduit between the first port and the breath transmission passage and first means for withdrawing fluid from the first port at a given flow rate; second means for interconnecting the breath transmission passage at a point near the second end to the second port, the second interconnecting means comprising a second connecting conduit between the second port and the breath transmission passage and second means for withdrawing fluid at the given rate from the second port; a source of bias gas connected to the third port; and means for generating a signal dependent upon the difference between the rate of gas flow through the first and second flow measurement passages responsive to patient inhalation from and exhalation to the breath transmission passage, characterized in that the flow resistance between the first end of the breath transmission passage and the third port approximately equals the flow resistance between the second end of the breath transmission passage and the third port, thereby balancing the signal generating means in the absence of flow through the breath transmission passage.

2. The spirometer of claim 1, in which the first and second ends of the breath transmission passage are unconnected to each other except for the connection through the elongated conduit.

3. The spirometer of claim 2, additionally comprising means for supplying fluid at a given rate to the first end of the breath transmission passage, and means for supplying fluid at the given rate to the second end of the breath transmission passage.

4. The spirometer of claim 1, in which the first and second ends of the breath transmission passage are connected together.

5. The spirometer of claim 4, additionally comprising means for supplying fluid at a given flow rate to the middle of the breath transmission passage.

6. The spirometer of claim 1, in which the breath transmission passage has a given cross-sectional area, and the first and second flow measurement passages have a substantially smaller cross-sectional area than the given cross-sectional area.

7. The spirometer of claim 1, in which the first and second interconnecting means each comprise a removable connection to permit substitution of a breath transmission passage having a different cross-sectional area.

8. The spirometer of claim 1, in which the signal generating means comprises a first elongated hot wire supported to extend along the length of the first flow measurement passage, a second elongated hot wire supported to extend along the length of the second flow measurement passage, a third elongated hot wire supported to extend along the length of the second flow measurement passage, a fourth elongated hot wire supported to extend along the length of the first flow measurement passage, a source of electrical excitation energy having first and second output terminals, means for connecting the first and second hot wires in series with the first hot wire connected to the first output terminal and the second hot wire connected to the second output terminal, and means for connecting the third and fourth hot wires in series with the third hot wire connected to the first output terminal and the fourth hot wire connected to the second output terminal, whereby the first and second hot wires and the third and fourth hot wires form a bridge having an output between the junction of the first and second hot wires and the junction of the third and fourth hot wires.

9. A spirometer comprising:
first, second, third, and fourth fluid flow passages connected in series to form a first junction between the first and second passages, a second junction between the second and third passages, and a third junction between the third and fourth passages;

means for sensing the fluid flow rate in the second passage;

means for sensing the fluid flow rate in the third passage;

a source of bias fluid connected to the second junction;

means for withdrawing fluid from the first junction at a given flow rate;

means for withdrawing fluid from the third junction at a given flow rate;

a first port connected to the first passage; and a second port connected to the fourth passage.

10. The spirometer of claim 9, in which the first and fourth passages are connected together to form a fourth junction therebetween.

11. The spirometer of claim 10, additionally comprising means for supplying fluid to the fourth junction.

12. The spirometer of claim 9, in which the first and fourth passages are unconnected to each other except for the connection through the second and third passages.

13. The spirometer of claim 9, additionally comprising means for supplying fluid to the first and fourth passages.

14. A spirometer comprising:

first, second, third, and fourth gas flow passages connected in series to form a first junction between the first and second passages, a second junction between the second and third passages, and a third junction between the third and fourth passages;

means for sensing the gas flow rate in the second passage;

means for sensing the gas flow rate in the third passage;

a source of gas supplying bias gas to the second junction at a substantially constant flow rate;

vacuum pump means for withdrawing gas from the first junction at a substantially constant flow rate and for withdrawing gas from the third junction at a substantially constant flow rate;

means for supplying patient gas at a substantially constant flow rate to the first and fourth passages;

a respirator;

a three-way valve having a first port connected to the respirator, a second port connected to the first passage, and a third port connected to the atmosphere; and a patient breath port connected to the fourth passage.

15. The spirometer of claim 14, in which the first and fourth passages are directly connected together to form a fourth junction therebetween, and the supplying means supplies gas to the fourth junction.

16. The spirometer of claim 15, in which the first and fourth passages are unconnected to each other except for the connection through the second and third passages.

* * * * *